US005616330A

United States Patent [19]

Kaufman et al.

[11] Patent Number: 5,616,330

[45] Date of Patent: Apr. 1, 1997

[54] STABLE OIL-IN-WATER EMULSIONS INCORPORATING A TAXINE (TAXOL) AND METHOD OF MAKING SAME

[75] Inventors: Robert J. Kaufman; Thomas J. Richard, both of University City; Ralph W. Fuhrhop, St. Louis, all of Mo.

[73] Assignee: HemaGen/PFC, St. Louis, Mo.

[21] Appl. No.: 276,899

[22] Filed: Jul. 19, 1994

[51] Int. Cl.[6] ........................ A61K 9/107; A61K 31/235; B01J 13/00

[52] U.S. Cl. .......................... 424/400; 252/312; 252/314; 514/511; 514/908; 514/938

[58] Field of Search .................................... 252/312, 314; 514/511, 908, 938; 424/400

[56] References Cited

U.S. PATENT DOCUMENTS

| | | | |
|---|---|---|---|
| 3,993,581 | 11/1976 | Yokoyama et al. | 252/312 |
| 4,073,943 | 2/1978 | Wretlind et al. | 514/938 X |
| 4,168,308 | 9/1979 | Wretlind et al. | 514/938 X |
| 4,784,845 | 11/1988 | Desai et al. | 514/938 X |
| 4,960,790 | 10/1990 | Stella et al. | 514/449 |
| 5,004,756 | 4/1991 | Ogawa et al. | 514/938 X |
| 5,028,600 | 7/1991 | Jeppsson | 514/182 |
| 5,407,683 | 4/1995 | Shively | 514/938 X |

FOREIGN PATENT DOCUMENTS

| | | |
|---|---|---|
| 9407484 | 4/1994 | WIPO . |
| 9414415 | 7/1994 | WIPO . |

OTHER PUBLICATIONS

Derwent Publications Ltd., London, GB; AN 93-309115 (39) & JP, A, 05221852 (LTT Kenkyusho KK) 31 Aug. 1993.

Davis, S. S. et al., "Lipid Emulsions as Drug Delivery Systems", *Annals of the New York Academy of Sciences,* Dec. 22, 1987.

Seewaldt, V. et al., "Bowel Complications with Taxol Therapy", *Jounral of Clinical Oncology,* vol. 11, No. 6, Jun. 1193, p. 1198.

Rowinsky, E. K. et al., "Taxol: The First of the Taxanes, an Important New Class of Antitumor Agents", *Seminars in Oncology,* vol. 19, No. 5, Dec. 1992, pp. 646–662.

Bicher, A. et al., "The Absence of Cumulative . . . Colony Stimulating Factor", *Anti–Cancer Drugs,* vol. 4, 1993, pp. 141–148.

Paereboom, D. M. et al., "Successful Re–treatment With Taxol . . . Reactions", *Journal of Clinical Oncology,* vol. 11, No. 5, May 1993; pp. 885–890.

Tarr, B. D. et al., "A New Parenteral Emulsion for the Administration of Taxol", *Pharmaceutical Research,* vol. 4, No. 2, 1987.

Collins–Gold, L.C., "Parenteral Emulsions for Drug Delivery", *Advanced Drug Delivery Reviews,* 5, 1990, pp. 189–208.

Richheimer, S.L. et al., "High–Performance Liquid Chromatographic Assay of Taxol", *Analytical Chemistry,* vol. 64, No. 20, Oct. 15, 1992, pp. 2323–2326.

*Primary Examiner*—Richard D. Lovering
*Attorney, Agent, or Firm*—Wood, Herron & Evans, P.L.L.

[57] ABSTRACT

This invention is directed to a composition of a taxine in a stable oil-in-water emulsion for intravenous administration. The invention also relates to a method for incorporating a taxine into an oil and making a stable oil-in-water emulsion.

The composition includes a taxine, an oil, water and a surfactant. In a preferred embodiment, the taxine is taxol, the oil is safflower oil and the surfactant is lecithin, The taxine is incorporated into the oil by dissolving the taxine in a solution of an oil and a taxine co-solvent, such as isopropanol, for example. The co-solvent then is removed to form a solution of the taxine in oil. This solution may be dispersed in water with a surfactant to form a stable oil-in-water emulsion for intravenous administration.

35 Claims, No Drawings

STABLE OIL-IN-WATER EMULSIONS INCORPORATING A TAXINE (TAXOL) AND METHOD OF MAKING SAME

FIELD OF THE INVENTION

This invention relates to the class of compounds known as taxines and, more particularly, to formulations of taxines (taxol) for intravenous infusion.

BACKGROUND OF THE INVENTION

Taxol, a member of the class of compounds known as taxines, comes from the bark of the Pacific yew tree, *Taxus brevifolia,* and has been found useful in the treatment of various cancers. For example, taxol has been used in treating ovarian, breast, non-small cell lung, and head and neck carcinomas. David M. Peereboom et al., "Successful Re-Treatment with Taxol After Major Hypersensitivity Reactions", *Journal of Clinical Oncology,* 11 (5), pp. 885–890 (1993). One of the difficulties in administering taxol is that the drug is insoluble in water. The present state of the art in taxol formulation requires a 50:50 mixture of Cremophor-EL surfactant (polyoxyethylated castor oil) and ethanol in order to solubilize the drug. Unfortunately, this taxol formulation leads to a relatively high incidence of major hypersensitivity reactions (HSRs) upon intravenous administration. These HSRs have been attributed to the unusually high concentration of Cremophor-EL required to solubilize the taxol. Id.

There have been other attempts to provide a taxol formulation, the most successful of which has been incorporation of the drug into a liposomal formulation. However, this preparation suffers from the fact that it is difficult to achieve a quantitative incorporation of the drug into the liposomal compartment. Furthermore, the product must be lyophilized and stored as a powder because taxol precipitates from aqueous liposomal formulations within a week of storage. For this reason, the liposomal formulation must be freeze dried and reconstituted prior to use.

Attempts to formulate taxol in a stable lipid emulsion have been unsuccessful. Taxol is reported to be insoluble in lipid emulsions such as Intralipid®, which contains soybean oil, or Liposyn®, which contains a mixture of soybean and safflower oils. L. C. Collins-Gold et al., "Parenteral Emulsions for Drug Delivery", *Advanced Drug Delivery Reviews,* 5, pp. 189–208 (1990). Heating taxol in either soybean oil or safflower oil, even upon sonication, does not result in the dissolution of appreciable amounts of taxol, and addition of taxol to a lipid emulsion during the homogenization step meets with equally disappointing results. Emulsions incorporating up to 15 mg/ml of taxol have been formulated with triacetin, L-α-lecithin, Polysorbate 80, Pluronic F-68, ethyloleate and glycerol. However, these emulsions are highly toxic and unstable. B. Tarr et al., "A New Parenteral Emulsion for the Administration of Taxol", *Pharmaceutical Research,* 4, pp. 162–165 (1987).

Therefore, there is a clear need for a stable, easily prepared, biocompatible, efficacious formulation of a taxine such as taxol exhibiting minimal side effects.

SUMMARY OF THE INVENTION

This invention is directed to a composition of a taxine in a stable oil-in-water emulsion for intravenous administration. This invention also relates to a method for incorporating a taxine into an oil and making a stable oil-in-water emulsion.

The composition includes a taxine, an oil, water and a surfactant. More particularly, a taxine such as taxol is solubilized in the oil in an effective pharmaceutical amount for intravenous administration. The taxine and oil mixture forms a dispersed phase in the water. Other taxines include taxotere, spicatin and others as hereinafter disclosed.

The oil may be any of a number of oils such as mineral, vegetable, animal, essential and synthetic oils, or mixtures thereof. Preferably, the oil is an oil rich in triglycerides, such as safflower oil, soybean oil or mixtures thereof. Because taxol is more soluble in safflower oil than soybean oil, safflower oil is most preferred. The surfactant used may be any of a number of surfactants, and usually is a phospholipid such as lecithin.

Typically, the taxine is present in an amount of about 0.1% to about 1% by weight of the emulsion, while the oil is present in an amount of from about 1% to about 40% and the surfactant is present in an amount of about 0.5% to about 5% by weight of the emulsion.

If desired, the composition may further include various additives. For example, glycerin may be added to adjust the osmolarity of the composition. Most commonly, sufficient glycerin (typically 0.5–5% by weight) is added to attain an osmolarity of between 280 and 320 milliosomoles per liter, but more or less may be added to achieve a hyperosmolar or hypoosmolar solution, depending on the desired end use.

Other common additives such as xylitol, mannitol, dextrose or lactated Ringer's solution may be added to the formulation, again depending on the desired end use.

Sterols such as cholesterol, or long chain ($C_{14}$–$C_{22}$) alcohols may be optionally added as co-solubilization agents. If used, such agents typically represent about 1% or less by weight of the emulsion.

The taxine may be incorporated at various concentrations, with 5 mg taxine/mi of emulsion being a typical concentration.

The invention also is directed to a method of incorporating a taxine into an oil. The method includes dissolving a taxine in a solution of an oil and a co-solvent for the taxine, and removing the taxine co-solvent to form a solution of the taxine in oil. The taxine co-solvent enables the taxine to be solubilized in the oil and preferably is a short chain alcohol, such as methanol, ethanol or isopropanol. The alcohol may be removed by a number of different methods such as evaporation and the like.

A further aspect of the invention involves a method for formulating a taxine in a stable oil-in-water emulsion. After forming a taxine and oil solution, the solution is dispersed in water with a surfactant to form a stable oil-in-water emulsion.

An advantage of the inventive composition and methods is the formation of a stable taxine-in-oil emulsion. Another advantage is that the taxine formulation is efficacious yet exhibits minimal side effects. Furthermore, the inventive formulation may be easily prepared and is biocompatible with several common additives.

DETAILED DESCRIPTION OF THE INVENTION

A. Taxine

Taxine formulations of the invention include a taxine, an oil, water and a surfactant. The term "taxine" as used in the literature and herein is meant to include the alternative forms of nomenclature such as "taxane". Examples of taxines which may be used include taxol (paclitaxel); taxotere; spicatin; taxane-2, 13-dione, 5.beta., 9.beta., 10.beta.-trihydroxy-, cyclic 9, 10-acetal with acetone, acetate; taxane-2, 13-dione, 5.beta., 9.beta., 10.beta.-trihydroxy-,cyclic 9, 10-acetal with acetone; taxane-2.beta., 5.beta., 9.beta., 10.beta.-tetrol, cyclic 9, 10-acetal with acetone; taxane; cephalomannine-7-xyloside; 7-epi-10-deacetylcephalomannine; 10-deacetylcephalomannine; cephalomannine; taxol B; 13-(2',3'-dihydroxy-3'-phenylpropionyl)baccatin III; yunnanxol; 7-(4-Azidobenzoyl)baccatin III; N-debenzoyltaxol A; O-acetylbaccatin IV; 7-(triethylsilyl)baccatin III; 7, 10-Di-O-[(2,2,2-trichloroethoxy)carbonyl]baccatin III; baccatin III 13-O-acetate; baccatin diacetate; baccatin; baccatin VII; baccatin VI; baccatin IV; 7-epi-baccatin III; baccatin V; baccatin I; baccatin III; baccatin A; 10-deacetyl-7-epitaxol; epitaxol; 10-deacetyltaxol C; 7-xylosyl-10-deacetyltaxol; 10-deacetyltaxol-7-xyloside; 7-epi-10-deacetyltaxol; 10-deacetyltaxol; and 10-deacetyltaxol B.

B. Oil

The term "oil" is used herein in a general sense to identify a large class of physiologically acceptable substances whether of mineral, vegetable, animal, essential or synthetic origin. Thus, the term "oil" is used herein as applied to a wide range of substances that are quite different in chemical nature. In the classification of oils by type or function, for example mineral oil is derived from petroleum and includes aliphatic or wax-based hydrocarbons, aromatic hydrocarbons or mixed aliphatic and aromatic based hydrocarbons. Also included in the mineral classification are petroleum-derived oils such as refined paraffin oil, and the like. In the vegetable classification, oils are chiefly derived from seeds or nuts and include drying oils such as linseed and tung oil; semidrying such as safflower and soy bean oils; nondrying such as castor, cottonseed and coconut oils and edible soap stocks such as palm and coconut oils. In the animal classification, oils usually occur as fats in tallow, lard and stearic acid sources. The liquid animal types include fish oils, oleic acid, sperm oil, etc. and they usually have a high fatty acid content. Included are some vegetable oils, such as olive, cottonseed, corn and peanut, as well as some special fish oils such as cod-liver, haliver, shark liver, and so forth which are used largely as medicines for their high vitamin content. A liquid fatty oil such as a mono-, di-, or triglyceride, or a mixture thereof, is the preferred oil. Medium chain triglycerides also serve as useful oils according to this invention.

C. Surfactant

A surfactant is needed to form stable emulsions. Any suitable surfactant may be employed alone or in combination with other surfactants. For example, egg yolk phospholipids such as lecithin or Pluronics emulsifying agents may be used. Pluronics agents are block polymer polyols sold by Wyandotte, e.g., Pluronics F68, having a molecular weight of about 8,000, may be employed. Ethoxylates of cholesterol, diacyl glycerol and dialkyl ether glycerol are useful surfactants. Also, using backbones of cholesterol, diacyl glycerol or dialkyl ether glycerol, block copolymers are made by adding ethylene oxide, propylene oxide and ethylene oxide, in that order, in varying amounts to produce surfactants. The emulsions of this invention may contain alkylphosphoryl choline or alkylglycerophosphoryl choline surfactants described in Kaufman and Richard, U.S. Ser. No. 791,420, filed Nov. 13, 1991 now U.S. Pat. No. 5,314,325. Specific examples of these surfactants are 1,2-dioctylglycero-3-phosphoryl choline, 1,2-ditetradecylglycero-3-phosphoryl choline, 1,2-dihexadecylglycero-3-phosphoryl choline, 1,2-dioctadecylglycero-3-phosphoryl choline, 1-hexadecyl-2tetradecylglycero-3-phosphoryl choline, 1-octadecyl-2-tetradecylglycero-3-phosphoryl choline, 1-tetradecyl-2-octadecylglycero-3-phosphoryl choline, 1-hexadecyl-2-octadecylglycero-3-phosphoryl choline, 1-2-dioctadecylglycero-3-phosphoryl choline, 1-octadecyl-2-hexadecylglycero-3-phosphoryl choline, 1-tetradecyl-2-hexadecylglycero-3-phosphoryl choline, 2,2-ditetradecyl-1-phosphoryl choline ethane and 1-hexadecyltetradecylglycero-3-phosphoryl choline. The 1,3-dialkyl glycerophosphoryl choline surfactants as described in Kaufman and Richard, U.S. Ser. No. 08/228,224, filed Apr. 15, 1994 and now abandoned, may also be used. Mixtures of these novel surfactants with other known surfactants may also be employed. Anionic surfactants include alkyl or aryl sulfates, sulfonates, carboxylates or phosphates. Cationic surfactants include such as mono-, di-, tri- and tetraalkyl or aryl ammonium salts. Non-ionic surfactants include alkyl or aryl compounds, whose hydrophilic part consists of polyoxyethylene chains, sugar molecules, polyalcohol derivatives or other hydrophilic groups. Zwitter-ionic surfactants may have a combination of the above anionic or cationic groups, and whose hydrophobic part consists of any other polymer, such as polyisobutylene or polypropylene oxides.

D. Preferred Taxine Formulation and Method

A preferred taxine formulation according to the principles of the invention is prepared by dissolving taxol (paclitaxel) in an alcohol solution. If desired, the optional sterol co-additive, such as cholesterol, may be added to this same alcohol solution. This solution is then added to an equivalent volume of oil and mixed until clear. The alcohol is then removed by rotary evaporation or evaporation under a stream of nitrogen.

A phospholipid, such as egg yolk lecithin, is dispersed into water, which may optionally contain glycerin for the purpose of achieving the desired osmolarity. In fact, glycerin may be added to the aqueous phase at any point during processing. While continuing to stir the dispersion at high speed, the oil solution containing taxol (and cholesterol or glycerin if desired) is added to the dispersion, forming a crude emulsion. The resulting crude emulsion is refined by cycling through a homogenizer, resulting in a shelf stable, small particle size, non-toxic emulsion suitable for intravenous administration. These and other objectives of this invention will be further understood with reference to the following nonlimiting examples.

EXAMPLE 1

Preparation of Lipid Emulsions of Taxol

A solution of 15 mg taxol/ml and 20 mg cholesterol/ml in isopropanol was prepared. This solution was added to an equal volume of safflower oil, and the alcohol was removed, either by rotary evaporation or by evaporation under a stream of nitrogen. This resulted in a safflower oil solution containing 15 mg taxol/ml and 20 mg cholesterol/ml.

1.9 g egg yolk lecithin was dispersed in 61 ml water using an Ultraturrax high speed mixer. Stirring continued at high speed while 32 ml of the safflower oil solution containing taxol (15 mg/ml) and cholesterol (20 mg/ml) were slowly added to the dispersion. The resulting crude emulsion was refined by cycling through a homogenizer for 20 minutes at a pressure of 8000 pounds per square inch. A Microfluidizer homogenizer was used to allow for work at small volumes. However, standard homogenization equipment, such as Gaulin homogenizers are expected to work equally well since they are commonly used in the large scale preparation of fat emulsions used in parenteral nutrition.

The resulting aqueous emulsion had the composition shown in Table 1, column 1. In order to compare stabilities, four additional formulations were prepared by the same method, and the compositions of these emulsions also are shown in Table. 1.

TABLE 1

| EMULSION | 1 | 2 | 3 | 4 | 5 |
|---|---|---|---|---|---|
| Lecithin | 2.0% | 2.0% | 2.0% | 2.0% | 2.0% |
| Safflower Oil | 33.3% | 33.4% | 33.3% | 33.5% | 33.6% |
| Glycerin | 0.0% | 0.0% | 2.0% | 0.0% | 1.9% |
| Cholesterol | 0.67% | 0.67% | 0.67% | 0.0% | 0.0% |
| Taxol | 0.51% | 0.00% | 0.51% | 0.51% | 0.5% |

EXAMPLE 2

Stability of Lipid Emulsions of Taxol

The five different taxol formulations presented in Table 1 above were subjected to an accelerated aging study of six weeks duration at 40° C. Stability measurements included taxol concentration, pH, viscosity and mean particle size. The results of the study are presented in Tables 2A–E.

TABLE 2A

| EMULSION 1 | 0 WEEKS | 2 WEEKS | 4 WEEKS* | 6 WEEKS |
|---|---|---|---|---|
| Taxol % | 0.46 | 0.45 | 0.47 | 0.44 |
| pH | 7.38 | 6.80 | 5.13 | 6.88 |
| Osmolarity (mOsm/L) | | | | |
| Viscosity (cP) | 3.21 | 2.91 | 10.0 | 3.59 |
| Mean Particle Size (μm) | 0.367 | 0.317 | 0.740 | 0.360 |

*This particular 4 week sample is an outlier sample, as is confirmed by the values at 6 weeks.

TABLE 2B

| EMULSION 2 | 0 WEEKS | 2 WEEKS | 4 WEEKS | 6 WEEKS |
|---|---|---|---|---|
| Taxol % | 0.00 | 0.00 | 0.00 | 0.00 |
| pH | 8.01 | 6.98 | 7.06 | 6.36 |
| Osmolarity (mOsm/L) | | | | |
| Viscosity (cP) | 3.62 | 3.42 | 3.54 | 3.59 |
| Mean Particle Size (μm) | 0.268 | 0.237 | 0.326 | 0.317 |

TABLE 2C

| EMULSION 3 | 0 WEEKS | 2 WEEKS | 4 WEEKS | 6 WEEKS |
|---|---|---|---|---|
| Taxol % | 0.45 | 0.44 | 0.45 | 0.45 |
| pH | 6.65 | 7.07 | 7.02 | 6.56 |
| Osmolarity (mOsm/L) | 357 | 360 | 358 | 362 |
| Viscosity (cP) | 3.61 | 2.91 | 3.34 | 4.14 |
| Mean Particle Size (μm) | 0.308 | 0.368 | 0.348 | 0.322 |

TABLE 2D

| EMULSION 4 | 0 WEEKS | 2 WEEKS | 4 WEEKS | 6 WEEKS |
|---|---|---|---|---|
| Taxol % | 0.47 | 0.45 | 0.46 | 0.46 |
| pH | 7.83 | 7.22 | 6.84 | 6.51 |
| Osmolarity (mOsm/L) | | | | |
| Viscosity (cP) | 3.12 | 3.11 | 3.02 | 3.34 |
| Mean Particle Size (μm) | 0.322 | 0.295 | 0.315 | 0.315 |

TABLE 2E

| EMULSION 5 | 0 WEEKS | 2 WEEKS | 4 WEEKS | 6 WEEKS |
|---|---|---|---|---|
| Taxol % | 0.39 | 0.41 | 0.44 | 0.42 |
| pH | 8.06 | 7.29 | 6.73 | 6.88 |
| Osmolarity (mOsm/L) | 344 | 332 | 342 | 343 |
| Viscosity (cP) | 2.92 | 2.62 | 2.82 | 3.07 |
| Mean Particle Size (μm) | 0.291 | 0.278 | 0.299 | 0.308 |

The taxol concentration remained relatively constant throughout the course of the study. The differences between the charged amount of taxol (0.51%) and the amount listed in the stability studies is due to the difficulty in maintaining accurate water balance during the preparation of such small scale emulsions (the homogenizer tubing contains significant dead volume). In support of this contention, the high performance liquid chromatographic analysis of taxol, from which the stability values are derived, showed no evidence of significant taxol degradation over the entire course of the study. In addition, microscopic examination (1200× magnification) demonstrated that taxol had not precipitated or crystallized from the sample.

As is the case with all triglyceride emulsions used clinically, there was a mild, biologically insignificant reduction in pH as the samples aged. Viscosity showed no statistically significant variation and was well below the range of human blood (9–12 cP). In addition, particle size was relatively constant over time, further demonstrating the stability of the lipid emulsions of taxol.

EXAMPLE 3

Admixture With Common Clinical Fluids

For clinic utility of products intended for intravenous use, it is important to determine whether or not common additives such as 5% dextrose or lactated Ringer's solution can be co-administered or mixed with the products. To this end, separate samples of emulsions 4 and 5 of Table 1 were diluted with dextrose or lactated Ringer's solution at two different concentrations (1:1 and 1:4 dilutions), and the samples were held at 25° C. for 24 hours and subsequently analyzed for mean particle size by laser light scattering using a Brookhaven Model BI-90. Mean particle size values before and after add mixture are shown in Table 3. These results indicate that the liquid emulsions of taxol are very stable to admixture with fluids commonly used in the clinical environment.

TABLE 3

| | Before Mixing | 1:1 Dextrose | 1:4 Dextrose | 1:1 Lactated Ringer's | 1:4 Lactated Ringer's |
|---|---|---|---|---|---|
| Emulsion 4 | 0.295 | 0.313 | 0.322 | 0.329 | 0.309 |
| Emulsion 5 | 0.278 | 0.293 | 0.267 | 0.301 | 0.294 |

EXAMPLE 4

Toxicity of the Lipid Emulsion of Taxol Relative to the Traditional Taxol-Cremophor Formulation 15 white Sprague-Dawley rats were divided into three groups with five animals in each group. One group served as a control and received no treatment. The second and third groups were infused with the inventive lipid emulsion and the commercially available taxol-Cremophor formulation, respectively. Prior to administration, the emulsion and Cremophor formulation were diluted to a final concentration of 1 mg taxol/ml according to the package insert for "Taxol® (paclitaxel) for Injection Concentrate", using 0.9% saline. Then the treatment group animals were infused with a dose of 42 mg/kg (42 cc/kg of diluted material) over the space of ½ hour. The animals were monitored for survival, organ weights, hematology and clinical chemistry at 14 days post infusion. Survival and normalized organ weight (grams per 100 grams body weight) data are displayed in Table 4.

TABLE 4

| | Survival | Liver | Lung | Spleen | Testes | Thymus |
|---|---|---|---|---|---|---|
| Control | 5/5 | 4.45 | 0.49 | 0.32 | 1.09 | 0.29 |
| Emulsion | 4/5 | 4.78 | 0.52 | 0.52 | 0.72 | 0.15 |
| taxol-Cremophor Formulation | 0/5 | | | | | |

All animals in the taxol-Cremophor formulation treatment group were ataxic and unresponsive to stimuli immediately upon infusion, and all were dead within 24 hours. In sharp contrast, all animals from the emulsion group exhibited normal behavior from the point of infusion onward. However, the animals in this group did exhibit weight loss during the first few days, and one of them died approximately four days after infusion. In comparing the weights of the emulsion treatment group with those of the control, the liver and lung weights all are within experimental error for different lots of animals. However, it appears that the spleens are slightly enlarged in the treatment group, while the testes and thymus are slightly smaller.

Blood samples were withdrawn by heart stick from the animals treated with the lipid emulsion, and the samples were analyzed for hematological and clinical chemistry parameters, with the results shown in Tables 5 and 6 respectively. The hematological and clinical chemistry results were within normal limits for a random rodent population. Surprisingly, the expected taxol-induced thrombocytopenia was not observed. It may be that the platelet population was restored over the extended 14 day time of the study.

TABLE 5

| HEMATOLOGY | | | | | | | |
|---|---|---|---|---|---|---|---|
| WBC ($th/mm^3$) | RBC ($mil/mm^3$) | HGB (g/dl) | HCT (vol %) | MCV $\mu m^3$ | MCH (pg) | MCHC (%) | Neut. ($\#/mm^3$) |
| 7325 | 5.43 | 12.0 | 36.1 | 66.5 | 22.2 | 33.5 | 1558 |
| Bands ($\#/mm^3$) | Lymphs ($\#/mm^3$) | Monos ($\#/mm^3$) | Eos ($\#/mm^3$) | Basos ($\#/mm^3$) | nRBC ($\#/mm^3$) | Platelets ($\#/mm^3$) | Retics ($\#/mm^3$) |
| 78 | 5522 | 74 | 0 | 0 | 0 | 1427000 | 290460 |

TABLE 6

| CLINICAL CHEMISTRY | | | | | | | |
|---|---|---|---|---|---|---|---|
| Glucose (mg/dl) | Nitrogen (mg/dl) | Creat (mg/dl) | Na (mEq/L) | K (mEq/L) | Cl (mEq/L) | Ca (mg/dl) | P (mg/dl) |
| 232 | 21 | 0.5 | 144 | 6.8 | 102 | 10.9 | 11.9 |
| UA (mg/dl) | Chol (mg/dl) | TG (mg/dl) | Bili (mEq/L) | BiliD (mEq/L) | BiliI (mEq/L) | AP (U/L) | SGOT (U/L) |
| 1.5 | 69 | 63 | 0.2 | 0.0 | 0.2 | 450 | 100 |
| SGPT (U/L) | GGTP (U/L) | LDH (U/L) | Protein (g/dl) | Albumin (g/dl) | Glob (g/dl) | A/G (ratio) | Fe ($\mu g/dl$) |
| 59 | <1 | 578 | 5.6 | 3.4 | 2.1 | 1.6 | 229 |

EXAMPLE 5

Efficacy

In order to test the efficacy of the lipid emulsion of taxol, the emulsion was screened against both the Cremophor excipient containing no taxol and the commercial taxol-Cremophor formulation. The three samples were tested in two different cell lines. The cell lines employed were mouse lymphocytic leukemia (L1210) in Fisher's medium containing 10% horse serum, and rat mammary adenocarcinoma (NMU) in MEM medium containing 10% fetal bovine serum. For each cell line, 10 ml of medium was inoculated with $10^6$ cells. The lymphocytic leukemia line was incubated for 16 hours, and the mammary adenocarcinoma line was incubated for 24 hours. After incubation, the cells were stained with Trypan blue, and the viable cells were counted with a hemacytometer. It is important to note that absorption techniques could not be employed because of the turbidity of the emulsion. In addition, agar diffusion was not applicable since emulsion particles diffuse at a different rate than the commercially formulated solution. The results for each line are presented in Tables 7A and 7B.

The data show that the Cremophor excipient containing no taxol is itself somewhat toxic to the cell lines employed. Otherwise, there appear to be no significant differences between the commercial taxol formulation and the inventive lipid emulsion of taxol.

TABLE 7A

| | MOUSE LYMPHOCYTIC LEUKEMIA | | |
|---|---|---|---|
| | Cremophor Excipient | Emulsion | taxol-Cremophor |
| 0.01 μg/ml | 121 | 45.1 | 52.8 |
| 0.1 μg/ml | 126 | 39.1 | 37.0 |
| 1.0 μg/ml | 147 | 33.1 | 36.2 |
| 10 μg/ml | 3.2 | 35.2 | 2.8 |

TABLE 7B

| | RAT MAMMARY ADENOCARCINOMA | | |
|---|---|---|---|
| | Cremophor Excipient | Emulsion | taxol-Cremophor |
| 0.01 μg/ml | 95.21 | 81.4 | 89.9 |
| 0.1 μg/ml | 91.7 | 36.8 | 40.8 |
| 1.0 μg/ml | 108 | 28.7 | 35.1 |
| 10 μg/ml | 48.0 | 20.8 | 24.8 |

Other modifications of this invention may be made without departing from its scope as will be understood to a person of ordinary skill in this art.

What is claimed is:

1. A composition for intravenous administration of taxine in a stable oil-in-water emulsion comprising:

a taxine;

a triglyceride;

water; and a surfactant, wherein said taxine is solubilized in said triglyceride in an effective pharmaceutical amount for intravenous administration, said taxine and triglyceride forming a stable dispersed phase in the water, said stable dispersed phase having a mean particle size of about 0.2 to about 0.4 μm upon aging said emulsion over a period of about six weeks at 40° C. as a measure of stability.

2. The composition of claim 1 wherein said taxine is selected from the group consisting of taxol; taxotere; spicatin; taxane-2, 13-dione, 5.beta., 9.beta., 10.beta.-trihydroxy-, cyclic 9, 10-acetal with acetone, acetate; taxane-2, 13-dione, 5.beta., 9.beta., 10.beta.-trihydroxy-, cyclic 9, 10-acetal with acetone; taxane-2.beta., 5.beta., 9.beta., 10.beta.-tetrol, cyclic 9, 10-acetal with acetone; taxane; cephalomannine-7-xyloside; 7-epi-10-deacetylcephalomannine; 10-deacetylcephalomannine; cephalomannine; taxol B; 13-(2',3'-dihydroxy-3'-phenylpropionyl)baccatin III; yunnanxol; 7-(4-Azidobenzoyl)baccatin III; N-debenzoyltaxol A; O-acetylbaccatin IV; 7-(triethylsilyl)baccatin III; 7,10-Di-O-[(2,2,2-trichloroethoxy)carbonyl]baccatin III; baccatin III 13-O-acetate; baccatin diacetate; baccatin; baccatin VII; baccatin VI; baccatin IV; 7-epi-baccatin III; baccatin V; baccatin I; baccatin III; baccatin A; 10-deacetyl-7-epitaxol; epitaxol; 10-deacetyltaxol C; 7-xylosyl-10-deacetyltaxol; 10-deacetyltaxol-7-xyloside; 7-epi-10-deacetyltaxol; 10-deacetyltaxol; and 10-deacetyltaxol B.

3. The composition of claim 1 wherein said taxine is selected from the group consisting of taxol and taxotere.

4. The composition of claim 1 wherein said taxine is taxol.

5. The composition of claim 1 wherein said tryglyceride is selected from the group consisting of safflower and soybean oils, and mixtures thereof.

6. The composition of claim 1 wherein said tryglyceride is safflower oil.

7. The composition of claim 1 wherein said surfactant is a phospholipid.

8. The composition of claim 7 wherein said phospholipid is lecithin.

9. The composition of claim 1 further including an additive selected from the group consisting of a sterol and a $C_{14}$–$C_{22}$ alcohol.

10. The composition of claim 9 wherein said sterol is cholesterol.

11. The composition of claim 10 wherein said cholesterol is present in an amount of about 0% to about 1% by weight of the emulsion.

12. The composition of claim 1 further including glycerin.

13. The composition of claim 12 wherein said glycerin is present in an amount of about 0% to about 5% by weight of the emulsion.

14. The composition of claim 1 wherein said taxine is present in an amount of about 0.1% to about 1% by weight of the emulsion.

15. The composition of claim 1 wherein said triglyceride is present in an amount of about 1% to about 40% by weight of the emulsion.

16. The composition of claim 1 wherein said surfactant is present in an amount of about 0.5% to about 5% by weight of the emulsion.

17. The composition of claim 1 wherein the emulsion contains dextrose or lactated Ringer's solution.

18. The composition of claim 1 wherein said taxine is incorporated into said emulsion at a concentration of about 5 mg taxine/ml of said emulsion.

19. A method of incorporating a taxine into an oil emulsion comprising the steps of:

dissolving a taxine in a solution of a triglyceride and a co-solvent for said taxine, removing said co-solvent to form a solution of said taxine in said triglyceride, forming an emulsion of said taxine and triglyceride solution in water, and homogenizing said emulsion to provide a stable oil-in-water emulsion.

20. The method of claim 19 wherein said taxine is selected from the group consisting of taxol; taxotere; spicatin; taxane-2, 13-dione, 5.beta., 9.beta., 10.beta.-trihydroxy-,cyclic 9, 10-acetal with acetone, acetate; taxane-2, 13-dione, 5.beta., 9.beta., 10.beta.-trihydroxy-, cyclic 9, 10-acetal with acetone; taxane-2.beta., 5.beta., 9.beta., 10.beta.-tetrol, cyclic 9, 10-acetal with acetone; taxane; cephalomannine-7-xyloside; 7-epi-10-deacetylcephalomannine; 10-deacetylcephalomannine; cephalomannine; taxol B; 13-(2',3'-dihydroxy-3'-phenylpropionyl)baccatin III; yunnanxol; 7-(4-Azidobenzoyl)baccatin III; N-debenzoyltaxol A; O-acetylbaccatin IV; 7-(triethylsilyl)baccatin III; 7,10-Di-O-[(2,2,2-trichloroethoxy)carbonyl]baccatin III; baccatin III 13-O-acetate; baccatin diacetate; baccatin; baccatin VII; baccatin VI; baccatin IV; 7-epi-baccatin III; baccatin V; baccatin I; baccatin III; baccatin A; 10-deacetyl-7-epitaxol; epitaxol; 10-deacetyltaxol C; 7-xylosyl-10-deacetyltaxol; 10-deacetyltaxol-7-xyloside; 7-epi-10-deacetyltaxol; 10-deacetyltaxol; and 10-deacetyltaxol B.

21. The method of claim 19 wherein said taxine is selected from the group consisting of taxol and taxotere.

22. The method of claim 19 wherein said taxine is taxol.

23. The method of claim 19 wherein said triglyceride is selected from the group consisting of safflower oil and soybean oil, and mixtures thereof.

24. The method of claim 19 wherein said triglyceride is safflower oil.

25. The method of claim 19 wherein said co-solvent is a short chain alcohol.

26. The method of claim 25 wherein said short chain alcohol is selected from the group consisting of methanol, ethanol and isopropanol.

27. The method of claim 19 wherein said co-solvent is removed by evaporation.

28. The method of claim 19 further comprising the step of adding a surfactant.

29. The method of claim 28 wherein said surfactant is a phospholipid.

30. The method of claim 29 wherein said phospholipid is lecithin.

31. The method of claim 19 comprising the further step of dispersing said taxine and triglyceride solution in water with a surfactant to form a stable oil-in-water emulsion.

32. The method of claim 31 wherein said triglyceride is selected from the group consisting of safflower oil and soybean oil, and mixtures thereof.

33. The method of claim 31 wherein said co-solvent is selected from the group consisting of methanol, ethanol and isopropanol.

34. The method of claim 31 wherein said triglyceride is safflower oil, said co-solvent is isopropanol and said surfactant is lecithin.

35. A method for incorporating taxol into a triglyceride emulsion comprising the steps of:

dissolving taxol in a solution of a triglyceride and a co-solvent for said taxol, removing said co-solvent by evaporation to form a solution of said taxol in said triglyceride, dispersing said taxol and triglyceride solution in water with a surfactant to form an emulsion, and homogenizing said emulsion to form a stable oil-in-water emulsion containing taxol.

* * * * *